(12) United States Patent
Bang et al.

(10) Patent No.: US 9,545,366 B2
(45) Date of Patent: Jan. 17, 2017

(54) HYDRATING COMPOSITION

(75) Inventors: Sang Lee Bang, Jersey City, NJ (US); Jodi Goldberg, Springfield, NJ (US); Carol Elmasry, South Amboy, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/599,732

(22) Filed: Aug. 30, 2012

(65) Prior Publication Data

US 2014/0065089 A1 Mar. 6, 2014

(51) Int. Cl.
*A61K 8/30* (2006.01)
*A61K 8/31* (2006.01)
*A61K 8/34* (2006.01)
*A61Q 19/00* (2006.01)
*A61K 8/92* (2006.01)

(52) U.S. Cl.
CPC .................. *A61K 8/31* (2013.01); *A61K 8/345* (2013.01); *A61K 8/922* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 7,351,417 B2 | 4/2008 | Barrow et al. | |
| 2007/0207113 A1* | 9/2007 | Joerger et al. | 424/70.31 |
| 2008/0260658 A1* | 10/2008 | Winter et al. | 424/47 |
| 2011/0097289 A1* | 4/2011 | Viala et al. | 424/63 |
| 2013/0122036 A1* | 5/2013 | Declercq | A61Q 19/00 424/195.17 |

FOREIGN PATENT DOCUMENTS

WO  WO 2006020163 A1 *  2/2006  ............. A61K 8/498

OTHER PUBLICATIONS

Sattayasamitsathit, S; Methacanon, P. and Prasertsan, P., 2011, Enhance 1,3-propanediol production from crude glycerol in batch and fed-batch fermentation with two-phase pH-controlled strategy, Electronic Journal of Biotechnology, vol. 14, No. 6. http://dx.doi.org/10.2225/vol14-issue6-fulltext-6.*

* cited by examiner

*Primary Examiner* — Nannette Holloman
(74) *Attorney, Agent, or Firm* — McNees Wallace & Nurick LLC

(57) ABSTRACT

The present invention is directed to a composition for hydrating keratinous substrates such as skin, hair and nails, the composition containing: (a) greater than 10% by weight of glycerin; (b) at least one C3-C8 alkanediol, other than glycerin; (c) an emollient mixture comprising shea butter and squalane; (d) at least one surfactant; and (e) water, all weights based on the total weight of the composition.

40 Claims, No Drawings

HYDRATING COMPOSITION

FIELD OF THE INVENTION

The present invention is directed to a hydrating composition and its method of use. More particularly, the invention is directed to a hydrating composition which does not require the use of a preservative to inhibit microbial decomposition of the composition, while at the same time providing the user with a pleasant aesthetic experience.

BACKGROUND OF THE INVENTION

For various reasons associated in particular with greater comfort of use (softness, emollience and the like), current cosmetic compositions are usually in the form of an emulsion of the oil-in-water (O/W) type consisting of an aqueous-dispersing-continuous phase and an oily-dispersed-discontinuous phase, or of an emulsion of the water-in-oil (W/O) type consisting of an oily-dispersing-continuous phase and an aqueous-dispersed-discontinuous phase. O/W emulsions are usually preferred in the cosmetics field, because O/W emulsions comprise an aqueous phase as external phase, which gives the emulsions, when applied to the skin, a fresher, less greasy and lighter feel than W/O emulsions.

Many compositions, especially cosmetic compositions, have been developed for easy and comfortable application onto a targeted substrate. Unfortunately, many of these compositions are in fact difficult to apply and do not possess a smooth feel upon application. Moreover, compositions often have a tendency to feel tacky, yielding poor application and spreadability characteristics.

This poor aesthetic experience if oftentimes further exacerbated by the use of high levels of glycerin, which is a fairly low cost humectant ingredient. Incorporating high levels of glycerin, generally greater than 10% by weight, yields a cosmetic composition that imparts a greasy and sticky feel onto a user's skin. The greasy and sticky feel is obviously undesirable to most, if not all, consumers. The use of synthetic texture modifiers such as silicone compounds, for example, may reduce the feeling of greasiness/stickiness. However, their use may not provide sufficient consumer appeal due to a residual feeling of tackiness, and results in the incorporation of synthetic ingredients which are, in general, disfavored by consumers over naturally-derived ingredients.

Also, for quite some time now, there has been a significant amount of negative publicity generated by the media surrounding the safety of parabens, a very commonly used class of preservatives. While parabens are recognized as being safe by the US Food and Drug Administration, some companies in the personal care industry have been substituting parabens with other, alternative, preservatives. Most preservatives, however, are synthetic and only a few of those are approved for use in natural formulas.

It is therefore an object of the present invention to provide a hydrating composition that does not require the use of parabens and/or synthetic preservatives, in general, to inhibit microbial decomposition.

It is another object of the present invention to provide a hydrating composition that is naturally-derived. It is yet another object of the present invention to provide a hydrating composition containing high levels of glycerin which is aesthetically pleasing and does not impart a tacky, sticky feel on a user's skin.

BRIEF SUMMARY OF THE INVENTION

The present invention is directed to a hydrating composition containing:
(a) greater than 10% by weight of glycerin;
(b) at least one C3-C8 alkanediol, other than glycerin;
(c) an emollient mixture comprising shea butter and squalane;
(d) at least one surfactant; and
(e) water, all weights being based on the total weight of the composition.

The present invention is also directed to a method of hydrating a keratinous substrate involving applying the above-disclosed hydrating composition onto the keratinous substrate.

DETAILED DESCRIPTION OF THE INVENTION

Other than in the operating examples, or where otherwise indicated, all numbers expressing quantities of ingredients and/or reaction conditions are to be understood as being modified in all instances by the term "about".

The hydrating composition and method of the present invention can comprise, consist of, or consist essentially of the essential elements and limitations of the invention described herein, as well as any additional or optional ingredients, components, or limitations described herein or otherwise useful in personal care compositions intended for topical application onto keratinous substrates.

"Keratinous substrate", as used herein includes, but is not limited to, skin, hair and nails.

"Naturally-derived", as used herein, means that at least about 99.5% of the composition is comprised of naturally-derived ingredients.

It has been surprisingly discovered by the inventors that a composition containing significant levels of glycerin, i.e. >10% by weight, can be formulated such that it imparts a pleasing tactile feel when applied onto a user's skin, i.e. not tacky, sticky, draggy feeling, and in the absence of any synthetic emollients and/or other synthetic ingredients, i.e. silicones.

Glycerin

The composition of the present invention contains greater than 10% by weight, preferably from about 15 to about 25% by weight, and most preferably from about 20 to about 23% by weight, of glycerin, all weights based on the total weight of the composition.

Alkanediols

Suitable alkanediols, other than glycerin, for use in the present invention include C3-C8 alkanediols. Examples thereof include, but are not limited to, neopentyl glycol, trimethylolpropane, pentaerythritol, sorbitol, sucrose, propylene glycol, propane diol, hexanediol, cyclohexanediol, butanediol, ethylene glycol, diethylene glycol, triethylene glycol, and polyethylene glycol. In a preferred embodiment, the alkanediols used are naturally derived from, for example, natural oils such canola oil, tall oil, soybean oil, safflower oil, linseed oil, corn oil, sunflower oil, olive oil, sesame oil, and combinations thereof.

The composition of the present invention contains from about 1 to about 10% by weight, preferably from about 2 to about 5% by weight, and most preferably from about 2 to about 4% by weight, of alkanediol, all weights based on the total weight of the composition.

A particularly preferred alkanediol for use in the present invention is a naturally-derived 1,3-propane diol, commercially available from Dupont Tate and Lyle Bio Products, under the tradename Zemea Propanediol®.

Emollient Mixture

The composition of the present invention further contains an emollient mixture comprising shea butter and squalane. The emollient mixture is present in the composition of the present invention in an amount of from about 5 to about 20% by weight, preferably from about 8 to about 15% by weight, and most preferably from about 10 to about 14% by weight, all weights based on the total weight of the composition.

Stated another way, the shea butter is present in the composition of the present invention in an amount of from about 1 to about 10% by weight, preferably from about 2 to about 8% by weight, and most preferably from about 4 to about 6% by weight, all weights based on the total weight of the composition.

Similarly, the squalane is present in the composition of the present invention in an amount of from about 1 to about 10% by weight, preferably from about 4 to about 8% by weight, and most preferably from about 5 to about 7% by weight, all weights based on the total weight of the composition.

Surfactant

The composition of the present invention further contains at least one surfactant present in an amount of from about 3 to about 15% by weight, preferably from about 5 to about 10% by weight, and most preferably from about 6 to about 8% by weight, all weights based on the total weight of the composition. The surfactant may be nonionic and/or cationic and is preferably carbohydrate-based. Examples thereof include, but are not limited to, plant-derived C6-C24 fatty alcohols (alkoxylates), C6-C24 glycosides, sorbitan esters, sucrose esters, and the like. A particularly preferred surfactant is cetearyl glucoside.

Water

The composition of the present invention further contains water present in an amount of from about 40 to about 70% by weight, preferably from about 45 to about 65% by weight, and most preferably from about 50 to about 55% by weight, all weights based on the total weight of the composition.

pH

It is imperative that the composition of the present invention have a pH ranging from about 3 to about 8, preferably from about 4 to about 7, and most preferably from about 5 to about 6. Various pH modifiers and/or buffering agents may be used in order to achieve the requisite pH. Examples thereof include, but are not limited to, acids such as citric and acetic acids, bases such as sodium and calcium hydroxide, and buffers comprising mixtures of acids and their salts. The pH modifiers and/or buffers are employed in the composition of the present invention only in an amount effective to achieve the desired pH level.

According to one embodiment, the composition of the present invention is free of preservatives, i.e. contains less than 2% by weight, based on the total weight of the composition, of conventional preservatives, particularly synthetic preservatives.

According to another embodiment, the composition of the present invention is free of parabens, i.e. contains less than 6 ppm by weight, based on the total weight of the composition, of parabens.

The composition of the present invention can also include hydrophilic and/or lipophilic active ingredients. Moreover, conventional additives may also be employed such as fragrances, dyestuffs, pigments, fillers and gelling agents.

The composition of the present invention is preferably made by a process involving at least two steps. The first step generally involves preparing an aqueous phase comprising water, glycerin and at least one glycol/alkanediol. The second step generally involves preparing an oily phase comprising the emollient mixture. The two phases are then combined via mechanical stirring/homogenization, during which time actives and/or additives may be added.

The present invention is also directed to a method of hydrating a keratinous substrate comprising applying the above-disclosed composition onto the substrate.

The present invention will be better understood from the examples which follow, all of which are intended for illustrative purposes only and are not meant to unduly limit the scope of the invention in any way.

EXAMPLES

An inventive composition in accordance with the present invention was formulated as per Table 1, below.

TABLE 1

| Ingredient | % Active |
| --- | --- |
| Nonionic surfactant | 7 |
| Emollient (shea butter + squalane) | 18 |
| Glycerin | 21 |
| Alkane diol | 3 |
| Water | 51 |
| Total | 100 |

The inventive composition of Table 1 was subjected to micro testing using the following protocol:

1. Product was inoculated with saline suspensions made out of 24 hour culture of bacteria and yeast isolates and 5 days culture of mold isolate:
    1.1.1 *Pseudomonas aeruginosa* 19429
    1.1.2 *Escherichia coli* 8739
    1.1.3 *Staphylococcus aureus* 6538
    1.1.4 *Enterococcus faecalis* 33186
    1.1.5 *Candida albicans* 10231
    1.1.6 *Aspergillus niger* 6275
2. Concentration of the suspension: approximately $1.0\ E+8$
3. Inoculation rate 1%
4. Final concentration in the product: approximately $1.0\ E+6$
5. Number of surviving microorganisms was monitored at 7, 14 and 28 days after inoculation by aerobic plate count method
6. Logarithmic reduction was calculated from the theoretical initial concentration of microorganism in the product The results are found in Table 2, below.

TABLE 2

| Microorganism | Inoculum CFU/g | (8 wks/ 45° C.) 7 days | (8 wks/ 45° C.) 14 days | (8 wks/ 45° C.) 28 days |
| --- | --- | --- | --- | --- |
| *Escherichia coli* | 2.0E6 | <200 | <200 | <200 |
| *Pseudomonas aeruginosa* | 2.3E6 | <200 | <200 | <200 |
| *Staphylococcus aureus* | 1.8E6 | <200 | <200 | <200 |
| *Enterococcus faecalis* | 1.9E6 | <200 | <200 | <200 |
| *Candida* | 2.7E6 | <200 | <200 | <200 |

TABLE 2-continued

| Microorganism | Inoculum CFU/g | (8 wks/ 45° C.) 7 days | (8 wks/ 45° C.) 14 days | (8 wks/ 45° C.) 28 days |
|---|---|---|---|---|
| *albicans* |  |  |  |  |
| *Aspergillus niger* | 2.4E6 | 8.4E3 | <200 | <200 |

Based on the data in Table 2, the inventive composition was deemed to have passed micro testing.

The inventive composition of Table 1 was also subjected to a consumer test to gauge consumer perception with respect to its tactile properties. The inventive composition was applied once a day onto the skin of fifty-two (52) subjects, aged 1 month to 3 years, for a period of 4 weeks. The subject's parent/guardian was then asked to rate the inventive composition, on a scale of 1-9 (1 being most negative and 9 being most positive), with respect to various tactile properties. The average ratings, as well as the tactile properties tested, are found in Table 3, below.

TABLE 3

| Week 4 tactile property measured | Median rating N = 52 |
|---|---|
| Product absorbs quickly into skin | 7.5 |
| Product spreads easily on skin | 8.0 |
| Skin does NOT feel sticky after application | 8.0 |
| Skin does NOT feel greasy after application | 7.0 |

As can be seen from the data in Table 3, subjects had a very positive tactile experience using the inventive composition, even though the composition had an extremely high level of glycerin present therein.

What is claimed is:

1. A cosmetic composition, comprising a hydrating composition, the hydrating composition consisting of:
   (a) greater than 10% by weight of glycerin;
   (b) at least one C3-C8 alkanediol, other than glycerin;
   (c) an emollient mixture comprising shea butter and squalane;
   (d) at least one surfactant; and
   (e) water, all weights based on the total weight of the cosmetic composition,
wherein the cosmetic composition is free of synthetic texture modifiers and includes the property of providing a pleasing tactile feel.

2. The cosmetic composition of claim 1, wherein (a) is present in an amount of from about 15 to about 25% by weight, based on the weight of the cosmetic composition.

3. The cosmetic composition of claim 1, wherein (a) is present in an amount of from about 20 to about 23% by weight, based on the weight of the cosmetic composition.

4. The cosmetic composition of claim 1, wherein (b) is present in an amount of from about 1 to about 10% by weight, based on the weight of the cosmetic composition.

5. The cosmetic composition of claim 1, wherein (b) is present in an amount of from about 2 to about 5% by weight, based on the weight of the cosmetic composition.

6. The cosmetic composition of claim 1, wherein (b) is 1,3-propanediol.

7. The cosmetic composition of claim 1, wherein (c) is present in an amount of from about 5 to about 20% by weight, based on the weight of the cosmetic composition.

8. The cosmetic composition of claim 1, wherein (c) is present in an amount of from about 8 to about 12% by weight, based on the weight of the cosmetic composition.

9. The cosmetic composition of claim 1, wherein the shea butter is present in an amount of from about 1 to about 10% by weight, based on the weight of the cosmetic composition.

10. The cosmetic composition of claim 1, wherein the shea butter is present in an amount of from about 2 to about 8% by weight, based on the weight of the cosmetic composition.

11. The cosmetic composition of claim 1, wherein the squalane is present in an amount of from about 1 to about 10% by weight, based on the weight of the cosmetic composition.

12. The cosmetic composition of claim 1, wherein the squalane is present in an amount of from about 4 to about 8% by weight, based on the weight of the cosmetic composition.

13. The cosmetic composition of claim 1, wherein (d) is present in an amount of from about 3 to about 15% by weight, based on the weight of the cosmetic composition.

14. The cosmetic composition of claim 1, wherein (d) is present in an amount of from about 5 to about 10% by weight, based on the weight of the cosmetic composition.

15. The cosmetic composition of claim 1, wherein (e) is present in an amount of from about 40 to about 70% by weight, based on the weight of the cosmetic composition.

16. The cosmetic composition of claim 1, wherein (e) is present in an amount of from about 45 to about 65% by weight, based on the weight of the cosmetic composition.

17. The cosmetic composition of claim 1, wherein the cosmetic composition has a pH of from about 3 to about 8.

18. The cosmetic composition of claim 1, wherein the cosmetic composition has a pH of from about 4 to about 7.

19. The cosmetic composition of claim 1, wherein the cosmetic composition is free of preservatives.

20. The cosmetic composition of claim 1, wherein the cosmetic composition is free of parabens.

21. The cosmetic composition of claim 1, wherein the at least one C3-C8 alkanediol is derived from natural oils selected from the group consisting of canola oil, tall oil, soybean oil, safflower oil, linseed oil, corn oil, sunflower oil, olive oil, sesame oil, and combinations thereof.

22. A cosmetic composition, comprising a hydrating composition, the hydrating composition consisting of:
   (a) from about 20 to about 23% by weight of glycerin;
   (b) from about 2 to about 4% by weight, of 1,3-propane diol;
   (c) from about 10 to about 14% by weight, of an emollient mixture comprising:
      (i) from about 4 to about 6% by weight of shea butter; and
      (ii) from about 5 to about 7% by weight, of squalane;
   (d) from about 6 to about 8% by weight of cetearyl glucoside; and
   (e) from about 50 to about 55% by weight, of water, all weights based on the total weight of the cosmetic composition,
      wherein the cosmetic composition is free of synthetic texture modifiers and includes the property of providing a pleasing tactile feel.

23. The cosmetic composition of claim 22, wherein the cosmetic composition is free of preservatives.

24. The cosmetic composition of claim 22, wherein the cosmetic composition is free of parabens.

25. The cosmetic composition of claim 22, wherein the 1,3-propane diol is derived from natural oils selected from the group consisting of canola oil, tall oil, soybean oil, safflower oil, linseed oil, corn oil, sunflower oil, olive oil, sesame oil, and combinations thereof.

26. A method of hydrating a keratinous substrate, comprising applying onto the substrate a cosmetic composition comprising a hydrating composition, the hydrating composition consisting of:
   (a) greater than 10% by weight of glycerin;
   (b) at least one C3-C8 alkanediol, other than glycerin;
   (c) an emollient mixture comprising shea butter and squalane;
   (d) at least one surfactant; and
   (e) water, all weights based on the total weight of the cosmetic composition,
wherein the cosmetic composition is free of synthetic texture modifiers and includes the property of providing a pleasing tactile feel.

27. The method of claim 26, wherein the cosmetic composition is free of preservatives.

28. The method of claim 26, wherein the cosmetic composition is free of parabens.

29. The method of claim 26, wherein the 1,3-propane diol is derived from natural oils selected from the group consisting of canola oil, tall oil, soybean oil, safflower oil, linseed oil, corn oil, sunflower oil, olive oil, sesame oil, and combinations thereof.

30. The method of claim 26, wherein the cosmetic composition further comprises at least one additive selected from the group consisting of pH modifiers, buffering agents, hydrophilic active ingredients, lipophilic active ingredients, conventional additives, fragrances, dyestuffs, pigments, fillers, gelling agents, and combinations thereof.

31. The cosmetic composition of claim 1, wherein the cosmetic composition further comprises at least one additive selected from the group consisting of pH modifiers, buffering agents, hydrophilic active ingredients, lipophilic active ingredients, conventional additives, fragrances, dyestuffs, pigments, fillers, gelling agents, and combinations thereof.

32. The cosmetic composition of claim 22, wherein the cosmetic composition further comprises at least one additive selected from the group consisting of pH modifiers, buffering agents, hydrophilic active ingredients, lipophilic active ingredients, conventional additives, fragrances, dyestuffs, pigments, fillers, gelling agents, and combinations thereof.

33. A cosmetic composition comprising the components:
   (a) from about 20 to about 23% by weight of glycerin;
   (b) from about 2 to about 4% by weight of at least one C3-C8 alkanediol other than glycerin;
   (c) from about 10 to about 14% by weight, in combination, of shea butter and squalane;
   (d) from about 6 to about 8% by weight of a surfactant;
   (e) from about 50 to about 55% by weight, of water, all weights based on the total weight of the composition; and
   (f) one or more of additives selected from pH modifiers, buffering agents, hydrophilic active ingredients, lipophilic active ingredients, fragrances, dyestuffs, pigments, fillers, and gelling agents; and,
      wherein the cosmetic composition has a pH ranging from about 3 to about 8; and,
      wherein the cosmetic composition is free of synthetic texture modifiers and synthetic emollients and includes the property of providing a pleasing tactile feel.

34. A cosmetic composition according to claim 33, wherein one or more of the components selected from glycerin, alkanediol, shea butter, squalane, surfactant, and one or more additives is not synthetic.

35. A cosmetic composition according to claim 1, wherein one or more of the components selected from glycerin, alkanediol, shea butter, squalane, surfactant, and one or more additives is not synthetic.

36. A cosmetic composition according to claim 34, wherein an alkanediol is derived from natural oils selected from the group consisting of canola oil, tall oil, soybean oil, safflower oil, linseed oil, corn oil, sunflower oil, olive oil, sesame oil, and combinations thereof, and wherein a non-synthetic surfactant is selected from C6-C24 fatty alcohols obtained from plants.

37. A cosmetic composition according to claim 36, wherein an alkanediol is 1, 3 propanediol.

38. A cosmetic composition according to claim 36, wherein an non-synthetic surfactant is selected from C6-C24 fatty alcohols is cetearyl glucoside obtained from plants.

39. A cosmetic composition according to claim 34, wherein at least about 99.5% of the glycerin, the alkanediol, the shea butter, the squalane, and the surfactant components is not synthetic.

40. A cosmetic composition according to claim 1, wherein the composition is free of synthetic emollients.

* * * * *